(12) United States Patent
Cohen

(10) Patent No.: US 6,419,665 B1
(45) Date of Patent: Jul. 16, 2002

(54) MEN'S UNDERGARMENT FOR INCONTINENCE

(76) Inventor: Morton H. Cohen, 207 McMillen Ave., Beaver Falls, PA (US) 15010

(*) Notice: Subject to any disclaimer, the term of this patent is extended or adjusted under 35 U.S.C. 154(b) by 0 days.

(21) Appl. No.: 09/498,225

(22) Filed: Feb. 3, 2000

Related U.S. Application Data

(63) Continuation-in-part of application No. 09/139,047, filed on Aug. 24, 1998, now abandoned.

(51) Int. Cl.[7] ................................................. A61F 5/44
(52) U.S. Cl. .................... 604/349; 604/395; 604/385.09
(58) Field of Search ...................... 604/385.09, 385.14, 604/385.15, 385.19, 393–402, 346, 347, 349, 351, 353, 355, 544, 344; 2/403

(56) References Cited

U.S. PATENT DOCUMENTS

| 4,644,945 A | * | 2/1987 | Thorner ...................... 128/159 |
| 5,283,912 A | * | 2/1994 | Chung ............................ 2/403 |
| 5,649,913 A | * | 7/1997 | Cohen ........................ 604/353 |
| 5,735,837 A | * | 4/1998 | Ishikawa .................. 604/385.1 |
| 5,827,250 A | * | 10/1998 | Fujioka et al. .............. 604/349 |

* cited by examiner

Primary Examiner—John G. Weiss
Assistant Examiner—C. Lynne Anderson
(74) Attorney, Agent, or Firm—Carothers & Carothers

(57) ABSTRACT

A male undergarment for incontinence, including undergarment shorts having front and back panels with a waistband at the top of the garment and thigh encircling leg portions at the bottom of the shorts with a crotch portion between the leg portions. A pocket protection cage of resilient plastic material is provided with an opening at the top and is secured to the inside of the front panel of the shorts and is positioned for natural protrusion of the male penis of the wearer into this opening. This pocket protection cage has portions which are positioned at an angle whereby the device protrudes downwardly into one leg portion of the undergarment to the side of the crotch. A disposable, flexible and water tight pocket is removably retained in the cage and is also provided with a top opening that is secured for conforming to the top opening of the cage for protrusion of the penis into this top opening of the pocket. Absorbent material is provided in the pocket for absorbing urine and the entire pocket may be disposed of after use and replaced with a new pocket containing absorbent material.

3 Claims, 2 Drawing Sheets

MEN'S UNDERGARMENT FOR INCONTINENCE

CROSS REFERENCE

This application is a continuation-in-part of U.S. patent application Ser. No. 09/139,047, filed Aug. 24, 1998 now abandoned for MEN'S UNDERGARMENT FOR INCONTINENCE.

BACKGROUND OF THE INVENTION

This invention pertains to an undergarment for men with incontinence.

Adult male incontinence is a common condition which causes the incontinent person to suffer with discomfort and embarrassment caused by urine penetrating undergarments and staining outer garments or clothing.

The most common means of dealing with adult partial incontinence is with the use of adult disposable diapers. Other undergarments for male incontinence have also been developed, for example see the present inventor's U.S. Pat. No. 5,649,913 for MEN'S BOXER SHORTS FOR INCONTINENCE, issued on Jul. 22, 1997. However, to date, none of these devices are fully effective or convenient to use.

It is a principal object of the present invention to provide an undergarment for men with incontinence which eliminates these aforementioned disadvantages.

SUMMARY OF THE INVENTION

The male undergarment for incontinence of the present invention includes an undergarment having front and back panels with a waistband at the top and thigh encircling leg portions at the bottom of the undergarment and a crotch portion between the leg portions. The undergarment may be provided in many different forms, such as boxer shorts, long or short pajama pants, etc. A pocket protection cage of resilient material is provided with a top opening and secured inside of the front panel of the undergarment and positioned for natural protrusion of a male penis of the wearer into this opening. A retainer on the pocket cage is provided for retaining the male penis in position.

The pocket protection cage has portions thereof that are positioned at an angle whereby it protrudes downwardly into one of the leg portions to the side of the crotch portion of the undergarment. A disposable, flexible and watertight pocket is removably retained in the cage for disposal after use. The pocket is provided with a top opening secured for conforming to the top opening of the cage to permit the protrusion of the male penis into this top opening of the pocket. Absorbent material is provided in the pocket for absorbing the urine.

The retainer for the penis may include an elastic noose dimensioned for contracting around the male penis. The retainer may additionally or independently include a notch at the top opening of the pocket protection cage for receiving the penis therethrough. The cage is preferably constructed of plastic and may be removably secured from the front panel of the undergarment through the use of snaps or Velcro or the like so that the undergarment may be washed or replaced independently of the cage.

BRIEF DESCRIPTION OF THE DRAWINGS

Other objects and advantages appear hereinafter in the following description and claims. The following drawings show, for the purpose of exemplification, without limiting the invention or appended claims, certain practical embodiments of the present invention wherein:

DETAILED DESCRIPTION OF A PREFERRED EMBODIMENT

Figure 1:
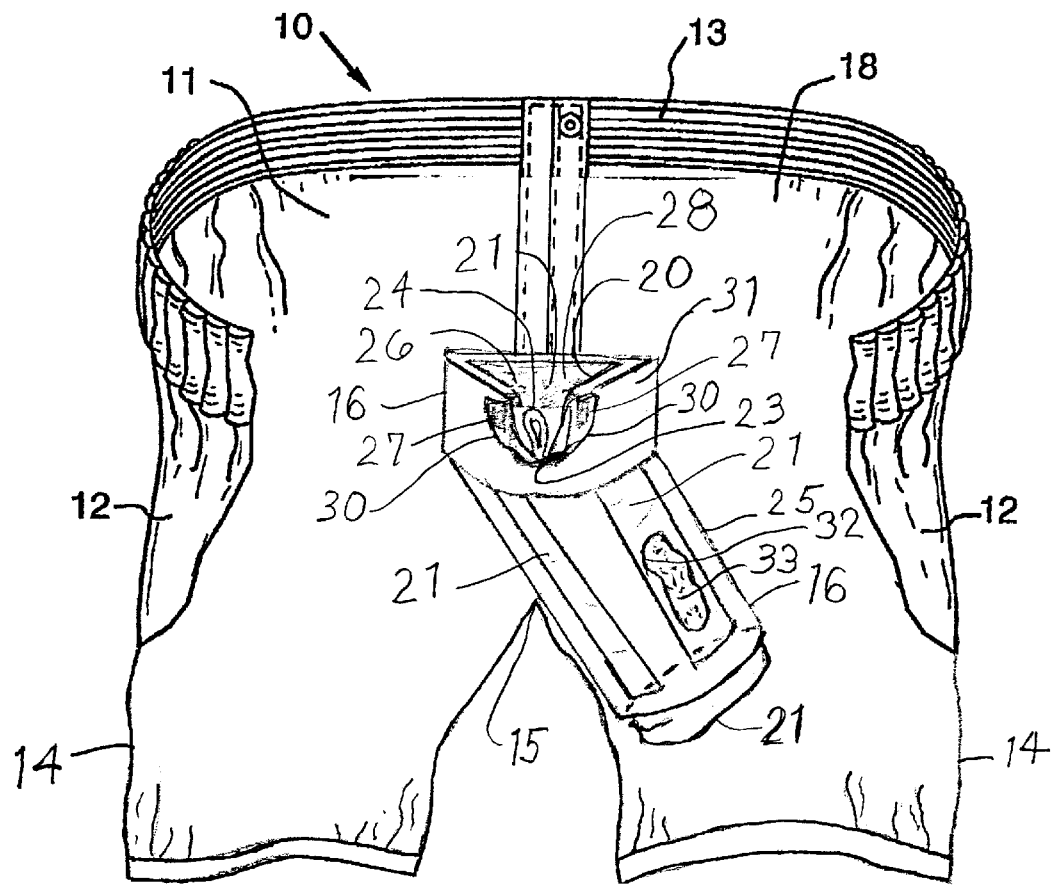
FIG. 1 shows an inside front view of the male undergarment of the present invention with portions of the back panel of the garment removed to permit internal viewing of the apparatus.
Figure 2:
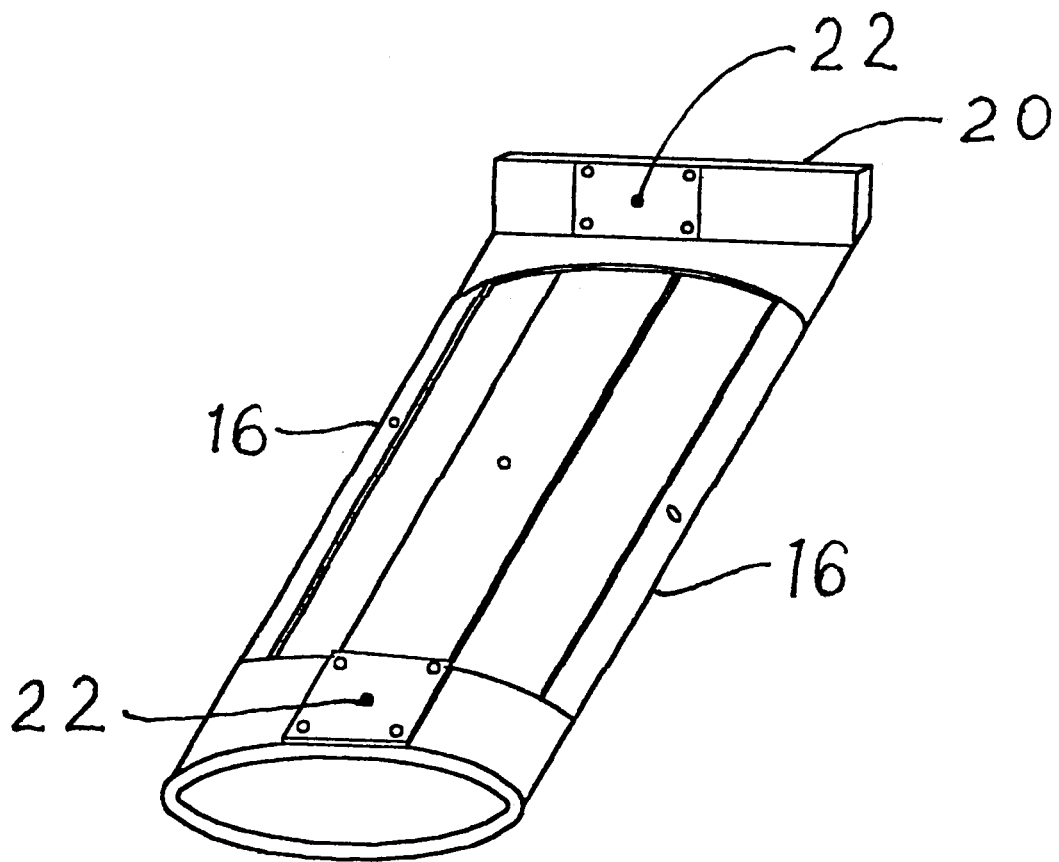
FIG. 2 is an enlarged view of the pocket protection cage portion of the apparatus of the present invention shown independently in back elevation.

Referring to the drawings, the mail undergarment 10 for incontinence is illustrated in accordance with the teachings of the present invention. It is shown in the form of men's boxer or undergarment shorts with a front panel 11, back panel 12, a waist band 13 at the top of the garment, thigh encircling leg portions 14 and a crotch portion 15 between the leg portions.

A pocket protection cage 16 is provided of resilient plastic material and has a top opening 20 and a hollow interior for receiving and protecting a disposable flexible and water tight bag or pocket 21, which in this instance is constructed of transparent thin film plastic.

Pocket protection cage 16 is secured to the inside of front panel 11 with snaps 22 and is positioned for natural protrusion of the male penis of a wearer into opening 20 through front notch 23 provided in the upper portion of cage 16. To further insure retention of the penis, an elastic noose 24 is also provided at the bottom of notch 23 and is dimensioned for contracting around the male penis.

Pocket protection cage 16 has portions 25 positioned at an angle whereby it protrudes into one of the leg portions, here the right hand leg portions 14, over to the side of the crotch portion 15. This permits the accommodation of a larger and longer pocket 21 for accumulation and retention of larger quantities of urine.

The disposable flexible and water tight pocket 21 is removably retained in cage 16 for disposal. Pocket 21 is secured at its upper end by use of Velcro strips 26 and 27 (snaps may be substituted) for conforming its top opening 28 to the top opening 20 of cage 16 so that the male penis may protrude into the top opening 28 of pocket 21.

The upper end of pocket 21 is split slightly for a short distance in order to accommodate notch 23 and either side of the slit portion of the pocket 21 are folded respectively left and right as flaps 30 and have Velcro fastener portions as indicated at 27 to secure the respective flaps 30 to the upper outside neck portion 31 of cage 16.

A portion 32 of pocket 21 is broken away to expose absorbent material 33 contained within pocket 16 for absorbing urine. This may be any suitable absorbent material, such as foams, sponges, wood fibers, cellulose, wadding or a super-absorbent polymer material, such as polyacrylate, or any suitable absorbent material on the market. the super-absorbent polymer materials are provided in the form of a powder which becomes solid or gel-like upon absorbing the urine and they fully contain all the moisture.

The pocket protection cage 16 prevents pocket 21 from being squashed or squeezed shut when the wearer is in a sitting position.

I claim:

1. A male undergarment for incontinence comprising:

an undergarment having front and back panels with a waist band at the top of the garment, thigh encircling leg portions at the bottom of the undergarment and a crotch portion between said leg portions;

a pocket protection cage of resilient material having a top opening and removably secured to the inside of the front panel and positioned for natural protrusion of a male penis of a wearer into said opening;

a retainer on said pocket cage for retaining a male penis in position;

said pocket protection cage having portions thereof positioned at an angle whereby it protrudes downwardly into one of said leg portions to a side of said crotch portion;

a disposable flexible and water tight pocket removably retained in said cage and having a top opening secured for conforming to the top opening of said cage for protrusion of a male penis into the top opening of said pocket; and absorbent material in said pocket for absorbing urine.

2. The male undergarment of claim 1, said retainer including an elastic noose dimensioned for contracting around a male penis.

3. The male undergarment of claim 1, said pocket protection cage including a notch in the top opening of said cage for receiving a male penis.

* * * * *